(12) United States Patent
Li et al.

(10) Patent No.: US 8,753,620 B2
(45) Date of Patent: Jun. 17, 2014

(54) INJECTABLE BULKING COMPOSITIONS

(75) Inventors: Jianmin Li, Lexington, MA (US); Michael Madden, Princeton, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 13/587,159

(22) Filed: Aug. 16, 2012

(65) Prior Publication Data

US 2012/0308629 A1 Dec. 6, 2012

Related U.S. Application Data

(63) Continuation of application No. 11/125,297, filed on May 9, 2005, now Pat. No. 8,263,109.

(51) Int. Cl.
*A61K 31/765* (2006.01)
*A61Q 90/00* (2009.01)
*A61K 47/32* (2006.01)

(52) U.S. Cl.
CPC ............... *A61K 31/765* (2013.01); *A61K 47/32* (2013.01); *A61Q 90/00* (2013.01)
USPC ....... 424/78.18; 424/78.31; 424/9.4; 424/9.5; 424/9.6; 424/93.7; 424/400; 424/401

(58) Field of Classification Search
None
See application file for complete search history.

(56) References Cited

U.S. PATENT DOCUMENTS

| | | | |
|---|---|---|---|
| 3,993,057 | A | 11/1976 | Ramwell |
| 4,578,076 | A | 3/1986 | Luukkainen et al. |
| 4,927,806 | A | 5/1990 | Kramer et al. |
| 5,986,168 | A | 11/1999 | Noishiki |
| 6,156,049 | A | 12/2000 | Lovato et al. |
| 6,168,777 | B1 | 1/2001 | Greff et al. |
| 6,231,591 | B1 | 5/2001 | Desai |
| 6,277,391 | B1 | 8/2001 | Seo et al. |
| 6,461,296 | B1 | 10/2002 | Desai |
| 6,491,672 | B2 | 12/2002 | Slepian et al. |
| 6,494,844 | B1 | 12/2002 | Van Bladel et al. |
| 6,495,164 | B1 | 12/2002 | Ramstack et al. |
| 6,544,227 | B2 | 4/2003 | Sahatjian et al. |
| 6,565,530 | B2 | 5/2003 | Sahatjian et al. |
| 6,592,794 | B1 | 7/2003 | Bachrach |
| 6,642,274 | B1 | 11/2003 | Neal |
| 6,852,330 | B2 | 2/2005 | Bowman et al. |
| 7,166,570 | B2 | 1/2007 | Hunter et al. |
| 2001/0047147 | A1 | 11/2001 | Slepian et al. |
| 2002/0010150 | A1 | 1/2002 | Cortese et al. |
| 2002/0068089 | A1 | 6/2002 | Vogel et al. |
| 2002/0082610 | A1 | 6/2002 | Cioanta et al. |
| 2002/0115992 | A1 | 8/2002 | Utley et al. |
| 2002/0176893 | A1 | 11/2002 | Wironen et al. |
| 2003/0050638 | A1 | 3/2003 | Yachia et al. |
| 2003/0064998 | A1 | 4/2003 | Francois et al. |
| 2003/0093157 | A1 | 5/2003 | Casares et al. |
| 2003/0100830 | A1 | 5/2003 | Zhong et al. |
| 2003/0153983 | A1 | 8/2003 | Miller et al. |
| 2003/0171678 | A1 | 9/2003 | Batten et al. |
| 2004/0037813 | A1 | 2/2004 | Simpson et al. |
| 2004/0037887 | A1 | 2/2004 | Bourne et al. |
| 2004/0096514 | A1 | 5/2004 | Vogel et al. |
| 2005/0064008 | A1 | 3/2005 | Bucay-Couto et al. |
| 2005/0064045 | A1 | 3/2005 | Zhong et al. |

FOREIGN PATENT DOCUMENTS

| | | |
|---|---|---|
| EP | 0561373 | 9/1993 |
| EP | 1078636 A1 | 2/2001 |
| EP | 1197208 A1 | 4/2002 |
| EP | 1410810 A1 | 4/2004 |
| EP | 1607109 A1 | 6/2005 |
| GB | 811.717 | 4/1959 |
| WO | 8400548 | 2/1984 |
| WO | 0013717 | 3/2000 |
| WO | 0123529 A1 | 4/2001 |
| WO | 03005889 A2 | 1/2003 |
| WO | 03070805 A1 | 8/2003 |
| WO | 2004071546 A1 | 8/2004 |
| WO | 2004112854 A1 | 12/2004 |

OTHER PUBLICATIONS

C. Lowell Parsons, "Evidence-based strategies for recognizing and managing IC," Contemporary Urology, vol. 15, No. 2, Feb. 2003, pp. 22-35.
C. Lowell Parsons, "Gynecologic Presentation of Interstitial Cystitis as Detected by Intravesical Potassium Sensitivity," Obstetrics & Gynecology, vol. 98, No. 1, Jul. 2001, pp. 127-132.
C. Lowell Parsons, "The prevalence of interstitial cystitis in gynecologic patients with pelvic pain, as detected by intravesical potassium sensitivity," American Journal of Obstetrics and Gynecology, vol. 187, No. 5, Nov. 2002, pp. 1395-1400.
Levie, Mark D., MD, Highlights from the American Association of Gynecologic Laparoscopists 32nd Annual Meeting, Medscape Ob/GYN & Women's Health 8(2), Nov. 18-22, 2003, Las Vegas, NV.
Peterson, Lynne, Summary of American Urogynecologic Society meeting, Sep. 11-13, 2003, Hollywood, FL, Trends-in-Medicine, Sep. 2003, 6 pp.
Dmochowski, Roger R., "Advances in the Treatment of Stress Urinary Incontinence: Bulking Therapy," Reviews in Urology, vol. 7, Suppl. 1, 2005, pp. S1-S2.
Kerr, Lindsey A., "Bulking Agents in the Treatment of Stress Urinary Incontinence: History, Outcomes, Patient Populations, and Reimbursement Profile," Reviews in Urology, vol. 7, Suppl. 1, 2005, pp. S3-S11.
Herschorn, Sender, "Current Use of Injectable Agents for Female Stress Urinary Incontinence," Reviews in Urology, vol. 7, Suppl. 1, 2005, pp. S12-S21.

*Primary Examiner* — Daniel Sullivan
*Assistant Examiner* — Barbara Frazier
(74) *Attorney, Agent, or Firm* — Kacvinsky Daisak Bluni PLLC

(57) ABSTRACT

According to an aspect of the invention, injectable bulking compositions are provided which contain the following: (a) fibers that are configured to prevent migration to locations in the body remote from the injection site, for example, because they have a minimum length that is sufficiently large to prevent migration of the fibers and/or because they have surface features that stimulate host tissue response to lock the fibers in position and (b) a carrier in an amount effective to render the composition injectable.

20 Claims, No Drawings

INJECTABLE BULKING COMPOSITIONS

STATEMENT OF RELATED APPLICATIONS

This application is a continuation of co-pending U.S. patent application Ser. No. 11/125,297, filed May 9, 2008, entitled "Injectable Bulking Compositions" and is incorporated by reference herein in its entirety.

FIELD OF THE INVENTION

The present invention relates to injectable bulking compositions for medical and cosmetic applications, among others.

BACKGROUND OF THE INVENTION

Urinary incontinence, vesicourethral reflux, fecal incontinence, intrinsic sphincter deficiency (ISD) and gastro-esophageal reflux disease, are examples of disorders, among others, that have responded to treatments with augmentative materials. In addition, it is known to use augmentative materials for aesthetic improvement, including improvement of skin contour.

For instance, a common method for treating patients with urinary incontinence is via periurethral injection of a bulking material. One such bulking composition is a paste known commercially as POLYTEF or URETHRIN. This paste is comprised of a fifty-fifty (50-50) by weight mixture of a glycerin liquid with polytetrafluoroethylene (PTFE) particles and is sold by DuPont. Over a period of time, the glycerin dissipates into the body and is then metabolized or eliminated, reducing the effective volume of the bulking material. Consequently, to achieve the desired result, the surgeon can overcompensate for the anticipated loss of bulking material by injecting a significantly larger amount of material than is initially required. However, the eventual dissipation of the glycerin complicates the surgeon's ability to gauge the appropriate amount of bulking material to inject. Furthermore, in extreme circumstances, such overcompensation can lead to complete closure of the urethra, which could put the patient into temporary urinary retention. As a result, the surgeon may ultimately not inject enough bulking mixture into the patient, leading to the need for a second or even a third procedure to inject additional material.

An alternative to PTFE paste is a collagen gel such as CONTIGEN, available from C R Bard. The collagen gel is injected and forms a fibrous mass of tissue around the augmentation site. This fibrous mass, created by the collagen injection, however, also dissipates over time and is eventually eliminated by the patient's body. As a result, additional injections are periodically required.

Yet another alternative is a hard particle suspension. One such commercially available product is DURASPHERE available from Carbon Medical Technologies. These hard particles, carbon coated zirconium beads, are injected in a beta-glucan carrier. The beta-glucan is eliminated by the patient's body over time. Moreover, in many cases, migration of the particles after administration appears to reduce the bulking effect of the particles over time. As a result, additional injections may be required.

In this regard, methods of injecting bulking agents commonly require the placement of a needle at a treatment region, for example, peri-urethrally or transperineally. The bulking agent is injected into a plurality of locations, assisted by visual aids, causing the urethral lining to coapt. In cases where additional applications of bulking agent are required, the newly added bulking agent may need to be injected at a higher pressure than the pressure at which the initial bulking agent was injected.

From the above, it is apparent that there is a need for bulking compositions which do not require supplemental injections or which require less frequent supplemental injections.

SUMMARY OF THE INVENTION

These and other challenges are addressed by the present invention.

According to an aspect of the invention, injectable bulking compositions are provided which contain: (a) fibers that are configured to prevent migration to locations in the body remote from the injection site, for example, because they have a minimum length that is sufficiently large to prevent migration of the fibers and/or because they have surface features that stimulate host tissue response to lock the fibers in position, and (b) a carrier in an amount effective to render the composition injectable.

An advantage of the present invention is that bulking compositions are provided, which promote tissue growth subsequent to administration. This effect can be used, for example, to make up for the loss of biodegradable bulking materials, to reduce migration of biostable bulking materials, to increase the compliance of the body of the bulking, and so forth.

In addition, because the bulking compositions of the present invention comprise fibers, an oriented structure is created upon administration (e.g., due to the passage of the fibers through a narrow lumen, such as a needle, which encourages them into a parallel formation), which in turn encourages oriented tissue, such as scar tissue or collagen growth.

These and other aspects, embodiments and advantages of the present invention will become immediately apparent to those of ordinary skill in the art upon review of the Detailed Description and Claims to follow.

DETAILED DESCRIPTION OF THE INVENTION

According to an aspect of the present invention, injectable bulking compositions are provided, which comprise (a) fibers that are configured to prevent migration to locations in the body remote from the injection site, for example, because they have a minimum length that is sufficiently large to prevent migration of the fibers and/or because they have surface features that stimulate host tissue response to lock the fibers in position and (b) a carrier for the fibers, which is provided in an amount effective to render the composition injectable. The fiber size is also beneficially of sufficient length such that local migration at the point of injection is minimized.

Applications for bulking agents in accordance with the invention include the treatment urinary incontinence, vesicourethral reflux, fecal incontinence, intrinsic sphincter deficiency, and aesthetic shaping (e.g., treatment of skin contour deficiencies), among others. The injectable compositions of the invention can be introduced into the subject via a variety routes, including, for example, transabdominal, transperineal, transcutaneous, transvascular, transurethral, periurethral, transureteral, transoral, and transrectal routes of insertion. Other routes of injection may also be suitable, depending on the location of the tissue to be treated. Where urethral bulking is the goal, periurethral or transperineal routes are typically used. Subjects (also referred to as patients) include vertebrate subjects, typically mammalian subjects, and more typically human subjects.

As used herein, a "fiber" is an elongated particle having a length that is at least 10 times longer than the greatest width of the particle, typically at least 20 times longer, at least 50 times longer, at least 100 times longer, or even more. For instance, in the case of a cylindrical fiber, the length is at least 10 times the diameter, whereas in the case of a ribbon-shaped fiber, the length is at least 10 times the width of the ribbon, and so forth. Fibers in accordance with the present invention typically have lengths ranging from 0.5 to 5000 microns and a maximum width ranging from 0.05 to 500 microns, and they more typically have a length ranging from 1 to 1000 microns and a maximum width ranging from 0.1 to 10 microns. Fibers within this size range are available commercially from a wide variety of sources, or they can be formed using a number of known fiber forming techniques.

Without wishing to be bound by theory, it is believed that, due to their elongate nature, the fibers within the compositions of the present invention are injected into tissue in an oriented (e.g., substantially parallel) manner, thereby creating an oriented scaffold which acts as a guide for cell migration, cell attachment, cell growth and/or tissue deposition (e.g., collagen fiber deposition). In some embodiments, the surfaces of the fibers are textured to enhance these processes.

The compositions of the invention typically contain from 30 to 90 wt % fibers, more typically from 50 to 80 wt % fibers.

Materials useful for forming fibers in accordance with the present invention include inorganic and organic materials, which can be natural or synthetic, and can be biostable or biodisintegrable (e.g., biodegradable). By "biodisintegrable" is meant that the material undergoes dissolution, degradation (i.e., bond cleavage, such as hydrolysis) and/or other disintegration process upon injection into the body, although such disintegration processes can take place over a number of months or even years. Conversely, by "biostable" is meant that the material remains substantially intact upon injection into the body.

Suitable inorganic materials for forming fibers in accordance with the present invention can be selected from the following: silica-based materials, sometimes referred to as glass ceramics (e.g., silica and bioglass); calcium-phosphate-based materials (e.g., hydroxyapatite); metal oxides, including aluminum oxides and transition metal oxides (e.g., oxides of titanium, zirconium, hafnium, tantalum, molybdenum, tungsten, rhenium and iridium); metals; and carbon based ceramic-like materials such as substantially pure carbon, silicon carbide and carbon nitride.

Suitable organic materials for forming fibers in accordance with the present invention can be selected from the following materials, many of which are polymers: polymers and copolymers of vinyl monomers including polyvinyl alcohols, polyvinyl ketones, polyvinylcarbazoles, polyvinyl esters such as polyvinyl acetates, polyvinyl halides such as polyvinyl chlorides, ethylene-vinyl acetate copolymers (EVA), polyvinylidene chlorides, polyvinyl ethers such as polyvinyl methyl ethers, polyvinylpyrrolidone, vinyl aromatics such as polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk); silicone polymers and copolymers; poly(carboxylic acid) polymers and copolymers including polyacrylic and polymethacrylic acid, and salts thereof, ethylene-methacrylic acid copolymers and ethylene-acrylic acid copolymers, where some of the acid groups can be neutralized with either zinc or sodium ions (commonly known as ionomers); acrylate and methacrylate polymers and copolymers (e.g., n-butyl methacrylate); acetal polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polyamide polymers and copolymers including nylon 6,6, nylon 12, polycaprolactams, polyacrylamides and polyether block amides; polysulfone polymers and copolymers including polyarylsulfones and polyethersulfones; resins including alkyd resins, phenolic resins, urea resins, melamine resins, epoxy resins, allyl resins and epoxide resins; polycarbonates; polyacrylonitriles; polybenzimidazoles; polyesters including polyethylene terephthalates and aliphatic polyester polymers and copolymers of alpha-hydroxy acids such as polylactide (including d-,l- and meso forms), polyglycolide and poly(lactide-co-glycolide), epsilon-caprolactone, poly(lactide-co-caprolactone), polyhydroxybutyrate, polyhydroxyvalerate, poly(para-dioxanone), polymers of trimethylene carbonate (and its alkyl derivatives), 1,4-dioxepan-2-one, 1,5-dioxepan-2-one, and 6,6-dimethyl-1,4-dioxan-2-one; polyether polymers and copolymers including polyarylethers such as polyphenylene ethers, polyether ketones, polyether ether ketones, and polyalkyl oxides such as polyethylene oxide (PEO) and polypropylene oxide; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; waxes, such as paraffin wax; biopolymers, such as polypeptides, proteins and polysaccharides and fatty acids (and esters thereof), including collagen, dextranomer fibrin, fibrinogen, elastin, chitosan, gelatin, starch, glycosaminoglycans such as hyaluronic acid, as well as mixtures and further copolymers of the preceding.

Polymers for forming fibers for use in the present invention include homopolymers and copolymers (including alternating, random, statistical, gradient and block copolymers), which may be cyclic, linear or branched (e.g., the polymers may have star, comb or dendritic branched architecture). They may be natural or synthetic, they may be thermoplastic or thermosetting, and so forth.

Materials, such as the inorganic and organic materials described above, can constitute the entirety of the fibers or only a portion of the fibers (e.g., constituting one component of a blend of materials, constituting a coating layer over a substrate, constituting a substrate beneath a coating layer, and so forth).

The surface characteristics that stimulate host tissue response to lock the fibers in position include surface features, such as roughness and microscopic patterns, as well as coatings of therapeutic agents. The surface roughness and microscopic patterns will promote cell adhesion and therefore enhance host tissue response, whereas therapeutic agents may chemically or biologically promote certain types of desired host tissue responses, for example, promoting quick tissue ingrowth.

To render them injectable, fibers such as those described above are generally admixed with a carrier, which in turn can be formed using one or more carrier species. The carrier typically includes one or more liquid species, for example, water, one or more liquid organic species (e.g., glycerin or other alcohols), or a mixture of water and one or more liquid organic species. Additional species such as alginate, beta-glucan, cellulose, collagen, and so forth, may also be provided within the carrier to improve the properties of the carrier, for example, to improve carrier viscosity, carrier lubricity, etc.

In certain embodiments, the bulking compositions of the present invention are provided with one or more optional therapeutic agents. Therapeutic agents include small molecule therapeutics, biopolymer therapeutics (e.g., proteins, DNA encoding proteins, polysaccharides, and so forth) as well as cells. Therapeutic agents may be included singly or in combination.

These optional therapeutic agents may be included in the bulking compositions in amounts effective to achieve a variety of purposes, including promotion of tissue growth, thereby allowing them to increase the long term (i.e., a period of at least 6 months) tissue bulking effect of the compositions, promotion of fibroblast attachment, enhancement of cellular migration to the injection site, promotion of organized soft tissue formation, and combinations of these effects.

For example, where the fibers within the bulking compositions of the invention are biodisintegrable, the optional therapeutic agents can be used to increase tissue bulk to compensate for the disintegration of the fibers. In this connection, it is noted that certain biodisintegrable polymers, such as polylactide, polyglycolide, and poly(lactide-co-glycolide), among others, produce inflammation as they degrade due to pro-inflammatory breakdown products, which leads to bulking in the form of scar tissue formation. The rate and degree of biodisintegrable polymer breakdown can depend upon a number of factors including monomer content (e.g., choice of monomer or ratio of monomers, if a copolymer), degree of crystallinity, polymer architecture, exposed surface area, and so forth.

Where the fibers within the bulking composition are biostable, the fibers, along with any optional therapeutic agents, can work in tandem to provide effective bulking. Moreover, tissue growth may also be useful to lock the fibers into place, thereby reducing or preventing migration of the same within the tissue.

The one or more optional therapeutic agents can be provided in the compositions of the invention in a number of ways, for example, blended with the fibers in the compositions, provided as coatings on the fibers, provided within matrices that correspond to the fibers or portions of the fibers (e.g., within coatings on the fibers), and so forth.

A range of therapeutic agent loadings can be used in conjunction with the above dosage forms, with the effective amount of loading being readily determined by those of ordinary skill in the art and ultimately depending, for example, upon the nature of the therapeutic agent, the tissue into which the dosage forms are introduced, the presence of other components in the dosage form, and so forth.

Therapeutic agents for use in conjunction with the present invention include agents that promote proliferation of soft tissue, including the following: connective tissue (e.g., fibrous connective tissue for structural bulking, adipose tissue for cosmetic bulking, etc.), muscle tissue (e.g., skeletal muscle for tendon repair), nervous tissue (e.g., to attach damaged nerves to one another), and so forth. Frequently, this will involve migration, attachment and/or proliferation of various cells including the following: connective tissue cells such as fibroblasts, adipocytes, macrophages, lymphocytes, mast cells; muscle cells such as skeletal muscle fibers (cells), cardiac muscle cells, and smooth muscle cells; nerve cells such as peripheral ganglion cells and Schwann cells; epithelial tissue cells such as squamous epithelial cells, cuboidial epithelial cells, columnar epithelial cells, pseudostratified columnar epithelial cells, and transitional epithelial cells; and progenitor cells which mature into cells such as those above, such as totipotent, pluripotent, multipotent, and progenitor stem cells.

Hence, therapeutic agents that can be administered in accordance with the present invention include those that promote migration, attachment and/or growth of various cells, as well as the cells themselves or their progenitors, preferably derived from the subject to be treated. Therapeutic agents include drugs, growth factors, hormones, stem cells, and combinations thereof, among many others.

Specific beneficial therapeutic agents for the practice of the present invention include those that promote collagen production, such as proinflammatory agents and sclerosing agents.

Suitable proinflammatory agents can be selected, for example, from endotoxins, cytokines, chemokines, prostaglandins, lipid mediators, and other mitogens. Specific examples of known proinflammatory agents from which suitable proinflammatory agents can be selected include the following: growth factors such as platelet derived growth factor (PDGF), fibroblast growth factor (FGF), transforming growth factor (such as TGF-alpha and TGF-beta), epidermal growth factor (EGF), insulinlike growth factor (IGF), interleukins such as IL-1-(alpha or beta), IL-8, IL-4, IL6, IL-10 and IL-13, tumor necrosis factor (TNF) such as TNF-alpha, interferons such as INF-gamma, macrophage inflammatory protein-2 (MIP-2), leukotrienes such as leukotriene B4 (LTB4), granulocyte macrophage-colony stimulating factor (GM-CSF), cyclooxygenase-1, cyclooxygenase-2, macrophage chemotactic protein (MCP), inducible nitric oxide synthetase, macrophage inflammatory protein, tissue factor, phosphotyrosine phosphates, N-formyl peptides such as formyl-Met-Leu-Phe (fMLP), second mitochondria-derived activator of caspase (sMAC), activated complement fragments (C5a, C3a), phorbol ester (TPA), superoxide, hydrogen peroxide, zymosan, bacterial lipopolysaccharide, chitin, imiquimod, and carrageenan, as well as mixtures thereof.

Sclerosing agents are agents that irritate tissue causing it sclerose or scar. However, due to the presence of fibers in the compositions of the present invention, the promoted scar tissue tends to be more organized, compared to typical bulking materials. This organization increases the compliance of the new tissue. Consequently, the new bulking becomes more readily adopted as natural host tissue.

Suitable sclerosing agents for the practice of the invention can be selected, for example, from the following (which list is not necessarily exclusive of the pro-inflammatory list set forth above): inorganic materials such as talc, aluminum hydroxide (e.g., in slurry form), sodium hydroxide, silver nitrate and hypertonic saline, as well as organic compounds, including alcohols such as ethanol (e.g., 50% to absolute), acetic acid, trifluoroacetic acid, formaldehyde, dextrose, polyethylene glycol ethers (e.g., polidocanol, also known as laureth 9, polyethylene glycol (9) monododecyl ether, and hydroxypolyethoxydodecane), tetracycline, oxytetracycline, doxycycline, bleomycin, triamcinolone, minocycline, vincristine, iophendylate, tribenoside, sodium tetradecyl sulfate, sodium morrhuate, diatrizoate meglumine, prolamine diatrizoate, alkyl cyanoacrylates such as N-butyl-2-cyanoactyalte and methyl 2-cyanoacrylate, ethanolamine, ethanolamine oleate, bacterial preparations (e.g., corynebacterium and streptococcal preparations such as picibanil) and mixtures of the same, for instance, TES (mixture of 1% tetradecyl sulfate, 32% ethanol, and 0.3% normal saline) and alcoholic solutions of zein (e.g., Ethibloc, which contains zein, alcohol, oleum papaveris, propylene glycol, and a contrast medium), and ethanol/trifluoroacetic acid mixtures, among others.

Note that in some cases, the therapeutic agents can also function as carriers or as imaging contrast agents, which will now be discussed.

Non-invasive imaging is a valuable diagnostic tool. For example, imaging guidance, either internal or external, can be used to determine the location of the bulking agent that is introduced. Consequently, the compositions of the present invention also optionally contain an effective amount of one or more imaging contrast agents (i.e., substances that enhance the image produced by medical diagnostic equipment). Among currently available contrast agents are magnetic resonance imaging (MRI) contrast agents, ultrasonic imaging contrast agents, x-ray fluoroscopy contrast agents, nuclear medicine contrast agents, and others.

For example, x-ray based fluoroscopy is a diagnostic imaging technique that allows real-time patient monitoring of motion within a patient. To be fluoroscopically visible, devices and/or compositions are typically rendered more absorptive of x-rays than the surrounding tissue (e.g., radiopaque materials). In various embodiments of the invention, this is accomplished by the use of contrast agents. Examples of contrast agents for use in connection with x-ray fluoroscopy include metals, metal salts and oxides (particularly bismuth salts and oxides), and iodinated compounds. More specific examples of such contrast agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine.

Ultrasound and magnetic resonance imaging can provide two-and/or three-dimensional images of a portion of the body. Ultrasound and MRI are advantageous, inter alia, because they do not expose the patient or medical practitioner to harmful radiation and can provide detailed images of the observed area.

Ultrasound uses high frequency sound waves to create an image of living tissue. A sound signal is sent out, and the reflected ultrasonic energy, or "echoes," used to create the image. Ultrasound imaging contrast agents are materials that enhance the image produced by ultrasound equipment. Ultrasonic imaging contrast agents introduced into the compositions of the present invention can be, for example, echogenic (i.e., materials that result in an increase in the reflected ultrasonic energy) or echolucent (i.e., materials that result in a decrease in the reflected ultrasonic energy). Suitable ultrasonic imaging contrast agents for use in connection with the present invention include solid particles ranging from about 0.01 to 50 microns in largest dimension (e.g., the diameter, where spherical particles are utilized), more typically about 0.5 to 20 microns. Both inorganic and organic particles can be used. Examples include microparticles/microspheres of calcium carbonate, hydroxyapatite, silica, poly(lactic acid), and poly(glycolic acid). Microbubbles can also be used as ultrasonic imaging contrast agents, as is known in the imaging art.

Magnetic resonance imaging (MRI) produces images by differentiating detectable magnetic species in the portion of the body being imaged. In the case of 1H MRI, the detectable species are protons (hydrogen nuclei). In order to enhance the differentiation of detectable species in the area of interest from those in the surrounding environment, imaging contrast agents are often employed. These agents alter the magnetic environment of the detectable protons in the area of interest relative to that of protons in the surrounding environment and, thereby, allow for enhanced contrast and better images of the area of interest. For contrast-enhanced MRI, it is desirable that the contrast agent have a large magnetic moment, with a relatively long electronic relaxation time. Based upon these criteria, contrast agents such as Gd(III), Mn(II) and Fe(III) have been employed. Gadolinium(III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) have been employed as MRI contrast agents. Chelation of the gadolinium or other paramagnetic ion is believed to reduce the toxicity of the paramagnetic metal by rendering it more biocompatible, and can assist in localizing the distribution of the contrast agent to the area of interest. Further information can be found, for example, in U.S. Patent Application No. 20030100830 entitled "Implantable or insertable medical devices visible under magnetic resonance imaging," the disclosure of which is incorporated herein by reference.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An injectable bulking composition comprising: (a) fibers that are configured to prevent migration of the fibers to locations in the body remote from the injection site, wherein said fibers are biostable and comprise a synthetic organic polymer selected from poly(vinyl alcohol) homopolymers and copolymers, and ethylene-vinyl acetate copolymers, and (b) a carrier in an amount effective to render the composition injectable.

2. The injectable bulking composition of claim 1, wherein the majority of the fibers have a length that is at least 20 times longer than the greatest width of the fiber.

3. The injectable bulking composition of claim 1, wherein the majority of the fibers have a length that is at least 50 times longer than the greatest width of the fiber.

4. The injectable bulking composition of claim 1, further comprising a therapeutic agent in an amount effective to increase the long term tissue bulking effect of said composition, to increase fibroblast attachment, to attract cellular migration to the injection site, to promote the formation of organized soft tissue, or a combination of these effects.

5. The injectable bulking composition of claim 4, wherein said therapeutic agent comprises cells.

6. The injectable bulking composition of claim 4, wherein said therapeutic agent comprises cells selected from stem cells, fibroblast cells, and cardiac muscle cells.

7. The injectable bulking composition of claim 4, wherein said therapeutic agent comprises a proinflammatory agent.

8. The injectable bulking composition of claim 4, wherein said therapeutic agent comprises a sclerosing agent.

9. The injectable bulking composition of claim 4, wherein said therapeutic agent is selected from growth factors and hormones.

10. The injectable bulking composition of claim 1, wherein said composition contains from 50 to 80 wt % fibers.

11. The injectable bulking composition of claim 1, wherein a majority of said fibers have a maximum length that is less than 1000 microns.

12. The injectable bulking composition of claim 1, wherein said fibers have a length that is sufficiently large to prevent said migration.

13. The injectable bulking composition of claim 1, wherein said fibers have surface features that stimulate host tissue response so as to prevent said migration.

14. A method of treating urinary incontinence, comprising administering an effective amount of the composition of claim 1 to a subject's urethra.

15. A method of cosmetic bulking, comprising administering a cosmetically effective amount of the composition of claim 1 to a subject.

16. The injectable bulking composition of claim 1, further comprising an imaging contrast agent.

17. The injectable bulking composition of claim 16, wherein the imaging contrast agent is a magnetic resonance imaging (MRI) contrast agent.

18. The injectable bulking composition of claim 16, wherein the imaging contrast agent is an ultrasonic imaging contrast agent.

19. The injectable bulking composition of claim 16, wherein the imaging contrast agent is an x-ray fluoroscopy contrast agent.

20. The injectable bulking composition of claim 1, wherein the fibers range from 1 to 1000 microns in length.

* * * * *